United States Patent
Widmark et al.

(10) Patent No.: US 6,487,438 B1
(45) Date of Patent: Nov. 26, 2002

(54) ARRANGEMENT AND REFERENCE MEANS TO DIRECT A BEAM IN RADIATION THERAPY

(75) Inventors: Anders Widmark, Umea (SE); Per Bergstrom, Umea (SE); Per-Olov Loforth, Umea (SE)

(73) Assignee: Beampoint AB, Umea (SE)

( * ) Notice: Subject to any disclaimer, the term of this patent is extended or adjusted under 35 U.S.C. 154(b) by 0 days.

(21) Appl. No.: 09/381,249

(22) PCT Filed: Mar. 17, 1998

(86) PCT No.: PCT/SE98/00481

§ 371 (c)(1),
(2), (4) Date: Dec. 3, 1999

(87) PCT Pub. No.: WO98/41282

PCT Pub. Date: Sep. 24, 1998

(30) Foreign Application Priority Data

Mar. 18, 1997 (SE) .............................................. 9700984

(51) Int. Cl.[7] .................................................. A61B 6/00
(52) U.S. Cl. ..................... 600/431; 600/427; 600/429; 600/436; 606/130; 378/62; 378/64; 378/65; 378/68
(58) Field of Search ................................. 600/426, 427, 600/431, 424, 425, 429, 436, 2; 606/130; 378/910, 64, 65, 68

(56) References Cited

U.S. PATENT DOCUMENTS 5,211,164 A   5/1993   Allen
5,320,100 A * 6/1994   Herweck et al. ............ 128/654
5,354,314 A * 10/1994  Hardy et al. ................ 378/206
5,520,646 A   5/1996   D'Andrea
5,640,956 A * 6/1997   Getzinger ................ 128/653.1
5,651,043 A * 7/1997   Tsuyuki et al. ............... 378/65
6,236,875 B1 * 5/2001  Bucholz et al. ............. 600/407

FOREIGN PATENT DOCUMENTS

WO        WO93/14803        8/1993

OTHER PUBLICATIONS

Derwent's Abstract No. 94–14527/02, week 9402, Abstract of SU 1782615 (Radiological Studies Res Inst). Dec. 23, 1992.

* cited by examiner

Primary Examiner—George Manuel
Assistant Examiner—Jeoyuh Lin
(74) Attorney, Agent, or Firm—Darby & Darby

(57) ABSTRACT

Apparatus and method for the precision aiming of a radiation beam for treating an internal cancer tumor in a patient. The method of treatment includes introducing at least one reference marker into the patient in a defined and locatable position in relation to the cancer tumor. A defined point in the cross section of the beam is located by a sight that is compared to the position of the reference marker and adjusted to ensure that the treatment beam is directed precisely at the cancer tumor before the remaining doses of radiation are given to the patient. The device according to the invention includes equipment for emitting a treatment beam, a sight arranged in the path of the beam to define a point in the cross section of the beam, and a device to read the beam arranged to receive the beam that has passed through the patient and visualize the position of the at least one said reference marker and the position of the sight.

34 Claims, 2 Drawing Sheets

ARRANGEMENT AND REFERENCE MEANS TO DIRECT A BEAM IN RADIATION THERAPY

BACKGROUND

1. Field of the Invention

The present invention concerns an arrangement and a reference means for the precision aiming of a radiation beam for treating an internal cancer tumor.

2. Description of Related Art

During the last 40 years, radiation therapy of localized prostate cancer has been used as one of a number of treatment methods. The levels of radiation considered suitable for treatment fall within the interval 65–70 Gy. However, the occurrence of viable cancer cells even after such a level of treatment has been demonstrated. One way of dealing with these remaining cells is to increase the level of treatment, known as scaling up the dose, initially to the interval of 76–80 Gy or more.

However, because of the lack of precision of current techniques, radiation treatment also carries with it an increased risk of affecting organs adjacent to the tumor. In the area around the prostate, this means primarily an increased risk for side effects seen as damage to the rectum and the urinary bladder as these are normally found in the radiation field. The risk for damage is especially pronounced with high doses of radiation.

The preparations for the radiation treatment of prostate cancer can be described briefly in the following way. The patient undergoes computer tomography to determine the geometry and location of the prostate. The position of the prostate is shown by markings on the skin of the patient. These markings then constitute the directional points for the beams used in treatment.

Even if the geometry of the prostate is known, problems can arise during radiation treatment because the position of the prostate is not constant in relation to the pelvis or, for that matter, to the skin where the markings have been made. The patient's subcutaneous fat means that the markings can be displaced in relation to the pelvis, and different muscle contractions, such as those in the area around the prostate, can displace the prostate up to one centimeter in relation to the pelvis. Furthermore, variation in the contents of the intestine and the bladder can affect the position of the prostate. When added together, this has the effect that the field of radiation must have a margin of 1.5–2 cm around the determined position of the prostate, which means that the rectum and bladder can be subjected to radiation, thus limiting the possibility of giving very high doses of radiation.

Even though the problem has initially been described in connection with the treatment of prostate cancer, it should be emphasised that many aspects of the problem are common to the treatment of cancer tumors in other organs. This is especially true for tumors of the cervix, urinary bladder, stomach, intestinal tract, pancreas, mouth, throat, etc.

SUMMARY OF THE INVENTION

During radiation therapy, a treatment beam is emitted from equipment used for the treatment. Depending on the shape of the object to be treated, a cross-section of the treatment beam is chosen so that the treatment is restricted to a specified treatment area. If the treatment area is to be reduced to a size approximately the size of the object to be treated, it is of great importance that the beam strikes its target, the tumor, with great precision.

One objective of the present invention is to achieve the precise aiming of the direction of a treatment beam during the radiation treatment of internal cancer tumors so that the margins of the treatment beam can be reduced, thereby minimizing the effect on adjacent organs and tissue.

This objective is achieved with an arrangement and a reference device including equipment for emitting a treatment beam, a sight arranged in the path of the beam and a device to read the location of a sight relative to a reference marker located in the patient.

By using the invention, it is possible to describe the geometry of an organ based on one or more reference points that always occupy the same position with reference to the organ. In addition, the possibility to repeatedly direct the treatment beam with precision in relation to at least one said reference point so that the beam always strikes the cancer tumor with precision, is also achieved. As such, the beam does not need as large a safety margin as has been required until now, but can be assigned a profile that is more or less exactly identical with that of the object to be treated.

Before each treatment occasion, it is thus possible to check, adjust and verify that the cancer tumor really is in the path of the treatment beam.

Additional features and advantages of the invention will be made evident by the following detailed description of one preferred embodiment of the invention, which constitutes one example and as such does not limit the area of protection of the invention. Embodiments of the invention have further applications within general internal radiation treatment of cancer, as will be made evident below. To simplify understanding, the text contains references to the enclosed drawings, in which equivalent or similar parts are assigned the same designation.

DETAILED DESCRIPTION OF EMBODIMENTS OF THE INVENTION

Figure 1:
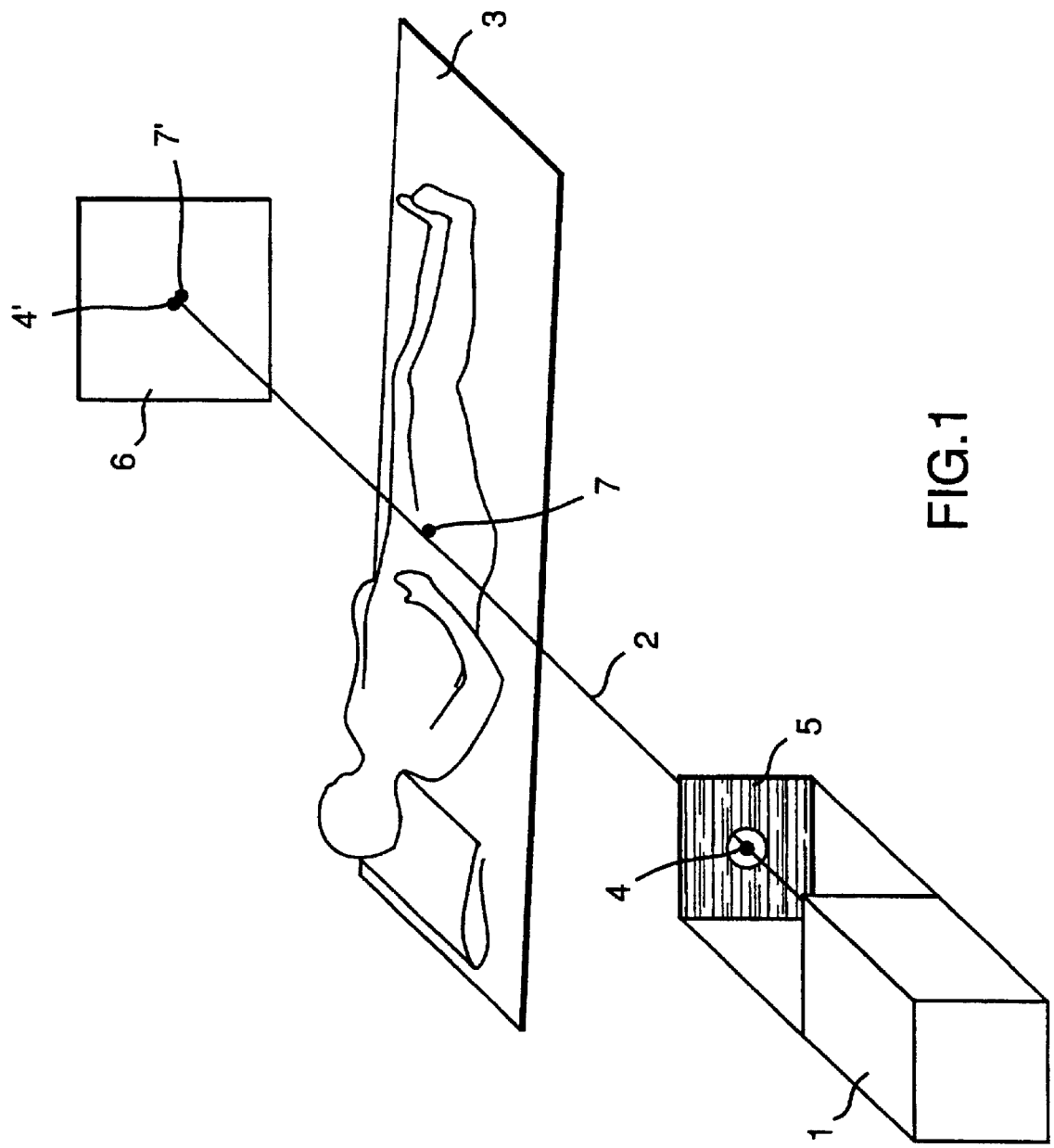
FIG. 1 shows schematically an arrangement according to one embodiment of the present invention.
Figure 2:
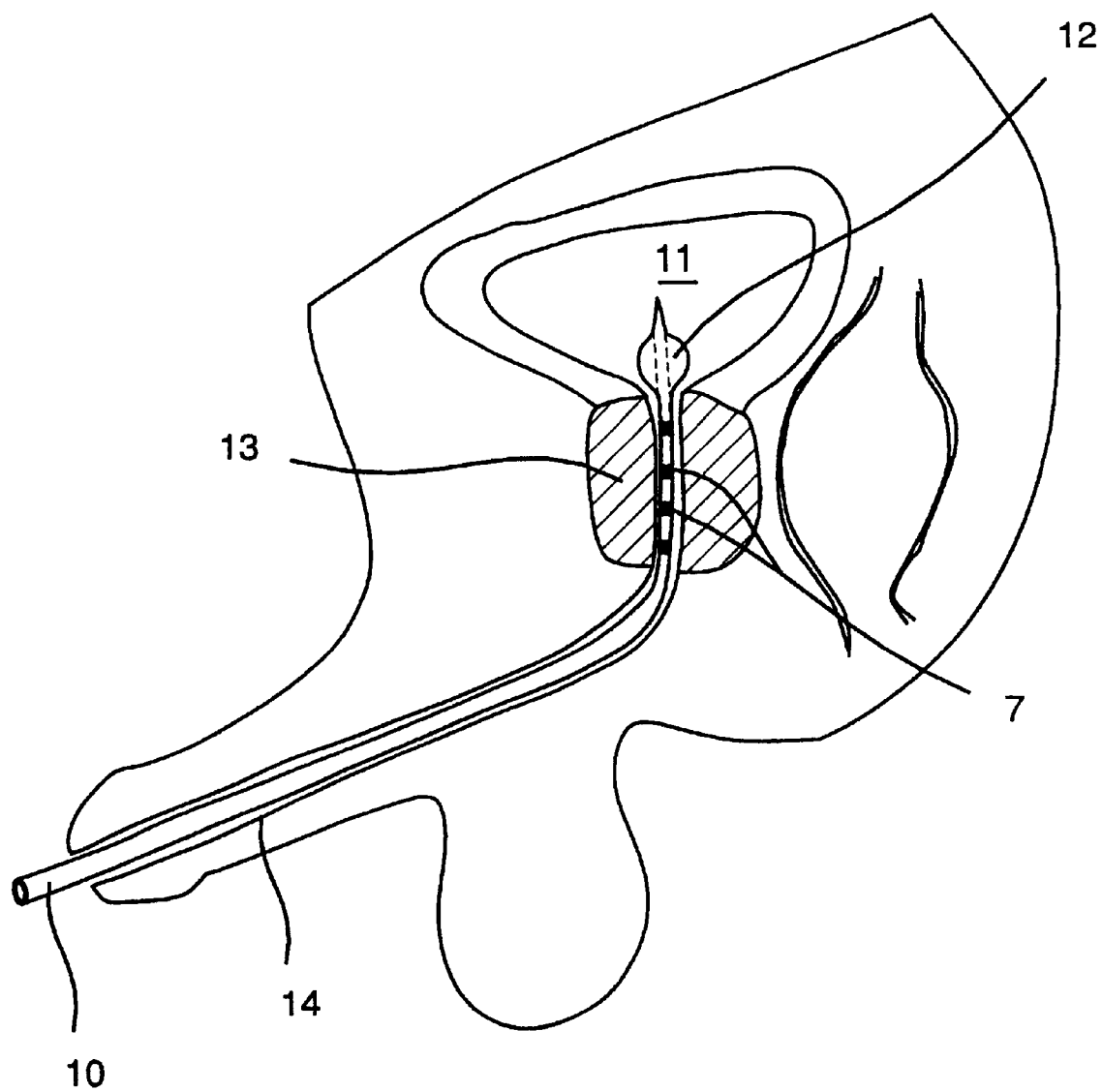
FIG. 2 shows schematically a reference device according to one embodiment of the present invention.

With reference to FIGS. 1 and 2, the manner in which we intend to use the arrangement is as follows. For the precision aiming of the direction of a treatment beam 2 against an internal cancer tumor of a patient, at least one reference marker 7 is introduced into the patient at a defined position in relation to the cancer tumor and, if possible, into the tumor itself. The geometry of the tumor is determined and the treatment is planned with reference to the reference marker 7. For the geometrical determination of the tumor, computer tomography/tomography, magnetic X-rays, or other suitable radiological techniques can be used with advantage, and the reference marker(s) can, for example, be composed of a liquid contrast agent, or a high density material such as lead, tantalum, tungsten or other material that is visible when computer tomography/tomography, magnetic X-rays, or other similar radiological techniques are used.

In addition, when the actual treatment is begun, the patient is brought into a treatment position and a set point in the cross-section of the beam is defined by a sight 4.

The geometrical determination and description of the cancer tumor is performed based on one or more reference markers 7 and, on the basis of that information, the cross-section of the treatment beam is built up and the position of the sight in the beam's cross-section is moved so that when the incidence of the beam corresponds with the cancer tumor, the positions of the sight and the reference markers coincide, even if they are located on separate elevations.

With at least one said reference marker in the defined position, the patient receives the first initial treatment, after which the relative positions of the reference marker or markers and the sight to one another are read with the help of, for example, the beam that passes through the patient. The relative positions can be adjusted later needed to ensure the precision of the direction of the beam towards the cancer tumor before the remaining doses in the treatment are given to the patient. By allowing the beam to project the position of the sight 4' and the position(s) of the marker(s) 7' on a sensitive surface 6, their relative positions to one another can be visualized.

It is desirable to keep the initial radiation dose low as radiation that misses the target does more harm than good. Experiments have shown that a dose equivalent to 0.03 Gy has been sufficient to visualize the reference marker and the sight on film. It is desirable to use a dose level that is less than 5% of the radiation dose used in treatment, preferably less than 2%.

When treating prostate cancer, for example, the reference marker can be introduced through the urinary tract by means of a catheter 10, as shown in FIG. 2. The reference markers need not be the same when determining the geometry of the cancer tumor and when treating it. The key factor is that the reference markers are located in known positions and in the same position in relation to the cancer tumor. To achieve this, the catheter 10 can be introduced through the urinary tract so that its free end enters the bladder 11 where an attachment arranged at the free end of the catheter, in this case a balloon device 12, is inflated inside the bladder to fix the position of the catheter in relation to the urinary tract, which is in turn essentially fixed in position relative to the prostate 13. The catheter is withdrawn slightly, which pulls the inflated balloon 12 against the floor of the bladder where it joins with the urinary tract. The actual reference marker 7 or reference markers 7 can be permanently positioned in the catheter or can be able to be introduced into the catheter in a defined position therein.

In addition to the said inflatable balloon, adjustable fold-out flaps that increase the local circumference, hooks or clips of different types or other similar locating devices suitable for reproducible location are also suggested as locating devices for the catheter or other carrier of the reference markers.

An arrangement according to the invention for performing the task includes what is, in fact, known treatment equipment 1 for emitting a treatment beam 2 and a device 3 for supporting the patient, whereby the patient has at least one reference marker 7 in relation to which the position of the cancer tumor is determined, a sight 4 arranged in the path of the beam to define a point in the cross-section of the beam, a device 6 to detect the beam arranged to receive the beam passing through the patient and visualize the position of at least one said reference marker 7' and the position of the sight 4', whereby the position of the beam in relation to the cancer tumor is determined.

The reading device 6 can be an X-ray film in a cassette suitable for high energy radiation.

The reading device 6 can even be one without film and instead include a receiving unit, a digital image processing system and a monitor for visualizing the cross-section of the treatment beam. It can be advantageous if the reading device uses what is known as a portal imaging system.

When a deviation from the desired agreement between the beam and the cancer tumor is registered, the device for adjusting the relative positions of the patient and the treatment equipment to one another is activated, either manually or automatically. This can occur, for example, by a change in the elevation or position of the device supporting the patient or by adjustment of the treatment equipment.

It is advantageous if the reference marker 7 or reference markers 7 are included in a reference device. The reference device then has at least one reference marker 7 in a material with high density and a position fixing-device.

The reference device can include several reference markers arranged at defined distances from each other. A marker can, for example, take the form of a dot, a line, an arc, a cross, a circle, etc.

The position-fixing device results in the marker(s) taking up a defined position in relation to the cancer tumor, preferably a reproducible set-up of the reference markers in a defined position in relation to the cancer tumor.

In one embodiment, the reference device includes a catheter 10 that has at its free end a reproducibly inflatable balloon, plus markers in the form of spheres arranged at defined positions along the catheter. The spheres are produced from a material of high density to enable visualisation in a high energy beam, preferably lead, tantalum and/or tungsten.

The catheter shown in FIG. 2 includes tubing 10 with several spheres 7 arranged in the internal channel of the tubing. The markers can naturally be arranged within the wall as spheres, rings, lines arcs, etc., to maintain an internal passage for, for example, urination. In this case, the use of several reference markers means that the catheter can be used by different patients with different anatomical measurements. For example, the third sphere can be used as a reference by one patient, whereas with another patient, the fourth sphere may be better placed to function as the reference point. A smaller channel passes through the tubing to the inflatable balloon 12 so that this can be expanded.

For certain treatments, it is not necessary to direct the beam at a point. Instead, a line can be judged to provide sufficient accuracy. For example, with a catheter with a wire or with several spheres arranged at a shorter distance from each other, the arc or line that the urinary tract forms through the prostate can be visualized and used to direct the beam.

Even if the text above to a large extent deals with the invention's application for the treatment of prostate cancer, it should be remembered that the invention also has uses with other types of cancer tumor.

In further applications of the invention, the reference marker can be introduced to, and kept in place by, surrounding body tissues, for example, in a cancer tumor.

For example, a marker provided with a clip or other attachment device can be arranged in a defined position in relation to a cancer tumor by means of, for example, surgery, peep-hole surgery or by the marker being introduced through one of the body's openings. The marker can then be kept in position throughout the whole cycle of treatment, from determining the position of the tumor to completed treatment, after which it can be removed by an appropriate means, such as the means by which it was introduced or, if made of material suitable for the purpose, be left in the body.

In those cases where a carrier is arranged to carry several reference markers with known positions relative to one another, it can be appropriate to arrange these in a pattern so that it is possible to determine where along the carrier the beam is directed. For example, the distance between the reference markers or their shape at a known position can deviate in a way that is easy to identify. The reference markers in a catheter can, for example, be arranged one cm apart, except for one position along the catheter where one marker is missing. In this way, the position of the beam along the carrier can be determined with increased certainty.

What is claimed is:

1. Arrangement for the precision aiming of a treatment beam against an internal cancer tumor in a patient into which at least one reference marker has been introduced and in relation to which the position of the cancer tumor is defined, the arrangement including treatment equipment for emitting a treatment beam with a defined cross-section, a patient support device for supporting the patient, a sight arranged in the path of the beam at a point in the cross-section thereof, and a reading device to read the beam, said reading device arranged to receive the beam that has passed through the patient for visualizing the position of the at least one reference marker and the position of the sight, whereby the position of the beam in relation to the cancer tumor can be determined.

2. Arrangement according to claim 1 wherein the at least one reference marker is of high density and the reading device includes a surface for the incident beam with a layer sensitive thereto, whereby the sight and the at least one reference marker can be visualized by projections thereof.

3. Arrangement according to claim 1, wherein the reading device is an X-ray film.

4. Arrangement according to claim 1, wherein the reading device includes a receiving unit, a digital image processing system and a monitor for visualizing the cross-section of the treatment beam.

5. Arrangement according to claim 1 further including an adjustment device for adjusting the positions of the patient and the treatment equipment relative to one another.

6. Arrangement according to claim 5, wherein the adjustment device is arranged in the patient support device.

7. A reference device for use with the arrangement of claim 1 including a plurality of reference markers arranged at defined distances from each other and a position fixing-device for the reproducible set-up of the reference markers in a defined position relative to the cancer tumor.

8. Reference device according to claim wherein 7, the reference device includes a catheter having the position fixing-device at its free end, the position fixing-device comprises an inflatable balloon, and at least one reference marker is arranged at a defined position along the catheter.

9. Reference device according to claim 8, wherein the catheter has a channel for maneuvering the inflatable balloon, a channel to allow urination, and wherein the reference markers are arranged within the wall of the catheter.

10. Reference device according to claim 7, wherein the reference markers are produced from a material of high density to enable visualization in a high energy beam.

11. Arrangement according to claim 10, wherein the reference markers are made of materials selected from the group consisting of lead, tantalum and tungsten.

12. Arrangement according to claim 1, wherein the reading device includes a portal imaging system.

13. Arrangement according to claim 1, further comprising a reference device for carrying a plurality of said reference markers arranged at defined distances from each other, the reference device also having a position fixing-device for the reproducible set-up of the reference markers in a defined position relative to the cancer tumor.

14. Arrangement according to claim 13, wherein the reference device comprises a catheter having the position fixing-device at its free end and at least one of the reference markers arranged at a defined position along the catheter.

15. Arrangement according to claim 14, wherein the position fixing-device is an inflatable balloon.

16. Arrangement according to claim 15, wherein the catheter includes a channel for maneuvering the inflatable balloon and a channel to allow urination, and wherein the reference markers arranged along the catheter are arranged within the wall thereof.

17. Arrangement according to claim 13, wherein the reference markers are produced from a material of high density to enable visualization thereof in a high energy beam.

18. Arrangement according to claim 17, wherein the reference markers are produced from materials selected from the group consisting of lead, tantalum and tungsten.

19. A method for aiming a treatment beam against an internal cancer tumor in a patient comprising:
   a) introducing at least one reference marker into the patient;
   b) determining the position of the tumor in relation to the reference marker;
   c) providing an arrangement including treatment equipment for emitting a treatment beam with a defined cross-section, a patient support device for supporting the patient, and a reading device to read the beam;
   d) arranging a sight in the path of the beam at a point in the cross-section thereof;
   e) passing a beam through the patient to the reading device to visualize the position of the at least one reference marker and the position of the sight;
   f) using the visualization to determine the position of the beam in relation to the cancer tumor; and
   g) adjusting the positions of the patient and the treatment equipment relative to each other to more precisely aim the beam against the cancer tumor if needed.

20. Method of claim 19, wherein the at least one reference marker is of high density and the reading device includes a surface for the incident beam with a layer sensitive thereto.

21. Method of claim 19, wherein the reading device is an X-ray film and the step of visualizing the position of the at least one reference marker and the position of the sight includes viewing their locations on the X-ray film.

22. Method of claim 19, wherein the reading device includes a receiving unit, a digital image processing system and a monitor.

23. Method according to claim 19, wherein the reading device includes a portal imaging system.

24. Method according to claim 19, wherein the step of adjusting the positions of the patient and the treatment equipment relative to each other comprises adjusting the position of the patient.

25. Method according to claim 19, further including the step of providing an adjustment device for adjusting the positions of the patient and the treatment equipment relative to each other.

26. Method of claim 25, wherein the step of providing an adjustment device comprises arranging the adjustment device in the patient support device.

27. Method of claim 19, wherein the step of introducing at least one reference marker into the patient includes providing a reference device having a plurality of reference markers arranged at defined distances from each other and a position fixing-device for the reproducible set-up of the reference markers in a defined position relative to the cancer tumor.

28. Method of claim 27, wherein the reference device includes a catheter having the position fixing-device at its free end, the position fixing-device comprises an inflatable balloon, and at least one reference marker is arranged at a defined position along the catheter.

29. Method of claim 28, wherein the catheter has a channel for maneuvering the inflatable balloon, a channel to allow urination, and wherein the reference markers are arranged within the wall of the catheter.

30. Method of claim 27, wherein the reference markers are produced from a material of high density.

31. Method of claim 30 wherein the reference markers are made of materials selected from the group consisting of lead, tantalum and tungsten.

32. Method of claim 19, wherein the step of passing a beam through the patient includes passing a beam having a dose level of no greater than about 5% of the dose level used for treating the cancer tumor.

33. Method of claim 32, wherein the step of passing a beam through the patient includes passing a beam having a dose level of no greater than about 2% of the dose level used for treating the cancer tumor.

34. Method of claim 19, wherein the step of passing a beam through the patient includes passing a beam having a dose equivalent to about 0.03 Gy.

* * * * *